United States Patent
Eder et al.

(10) Patent No.: US 9,702,983 B2
(45) Date of Patent: Jul. 11, 2017

(54) MULTI-SPOT COLLECTION OPTICS

(75) Inventors: Haim Eder, Kiryat Ono (IL); Nissim Elmaliach, Raanana (IL); Igor Krayvitz (Krivts), Rehovot (IL); Mario Mützel, Aalen (DE)

(73) Assignees: Applied Materials Israel, Ltd., Rehovot (IL); Carl Zeiss Microscopy GMBH, Jena (DE)

( * ) Notice: Subject to any disclaimer, the term of this patent is extended or adjusted under 35 U.S.C. 154(b) by 654 days.

(21) Appl. No.: 14/115,326

(22) PCT Filed: May 2, 2012

(86) PCT No.: PCT/US2012/036137
§ 371 (c)(1),
(2), (4) Date: Apr. 1, 2014

(87) PCT Pub. No.: WO2012/151288
PCT Pub. Date: Nov. 8, 2012

(65) Prior Publication Data
US 2014/0197322 A1    Jul. 17, 2014

Related U.S. Application Data (60) Provisional application No. 61/481,886, filed on May 3, 2011.

(51) Int. Cl.
*G01T 1/20* (2006.01)
*G01N 21/62* (2006.01)
(Continued)

(52) U.S. Cl.
CPC .......... *G01T 1/2002* (2013.01); *G01J 1/0425* (2013.01); *G01N 21/62* (2013.01); *H01J 37/244* (2013.01);
(Continued)

(58) Field of Classification Search
CPC .. G01N 21/886; G01N 21/956; G01N 21/474; G01N 21/00; G01N 2201/0833
See application file for complete search history.

(56) References Cited

U.S. PATENT DOCUMENTS

| | | | |
|---|---|---|---|
| 4,810,053 A | 3/1989 | Woith | |
| 6,465,783 B1 * | 10/2002 | Nakasuji | G01N 23/225 250/306 |

(Continued)

FOREIGN PATENT DOCUMENTS

| | | |
|---|---|---|
| JP | 2006-32278 | 8/2007 |
| JP | 2009-507351 | 2/2009 |

OTHER PUBLICATIONS

International Preliminary Report on Patentability dated Nov. 5, 2013 for PCT/US2012/036137.
(Continued)

*Primary Examiner* — David J Makiya
*Assistant Examiner* — Kenneth J Malkowski
(74) *Attorney, Agent, or Firm* — Lowenstein Sandler LLP (57) ABSTRACT

Apparatus for detecting optical radiation emitted from an array of spots on an object. The apparatus includes a plurality of light guides having respective input ends and output ends, with the input ends ordered in a geometrical arrangement corresponding to the array of the spots. Relay optics collect and focus the optical radiation from the object onto the input ends such that each input end receives the optical radiation from a corresponding one of the spots. Multiple detectors and each coupled to receive the optical radiation from an output end of a respective one of the light guides.

20 Claims, 6 Drawing Sheets

(51) Int. Cl.
    *H01J 37/244*  (2006.01)
    *H01J 37/28*   (2006.01)
    *G01J 1/04*    (2006.01)
    *G01N 21/25*   (2006.01)
    *G01N 21/64*   (2006.01)

(52) U.S. Cl.
    CPC ............ *H01J 37/28* (2013.01); *G01N 21/253* (2013.01); *G01N 21/6452* (2013.01); *G01N 2201/0833* (2013.01); *H01J 2237/2445* (2013.01); *H01J 2237/2446* (2013.01)

(56) References Cited

U.S. PATENT DOCUMENTS

| | | | |
|---|---|---|---|
| 6,507,685 B1* | 1/2003 | Polynkin | G01J 3/2803 |
| | | | 385/15 |
| 7,130,039 B2* | 10/2006 | Vaez-Iravani | G01N 21/95623 |
| | | | 356/237.5 |
| 7,623,229 B1 | 11/2009 | Vaez-Iravani et al. | |
| 7,626,696 B2 | 12/2009 | Zhang | |
| 2003/0020912 A1* | 1/2003 | Norton | G01B 11/02 |
| | | | 356/369 |
| 2007/0153265 A1 | 7/2007 | Vaez-Iravani et al. | |
| 2007/0228274 A1 | 10/2007 | Elyasaf et al. | |
| 2009/0114818 A1* | 5/2009 | Casares | H01J 37/045 |
| | | | 250/307 |
| 2010/0265498 A1 | 10/2010 | Zhang | |
| 2011/0069312 A1* | 3/2011 | Kandel | G01N 21/956 |
| | | | 356/369 |
| 2011/0096326 A1 | 4/2011 | Crafts et al. | |

OTHER PUBLICATIONS

Extended European Search Report dated Oct. 29, 2014 for Application No. EP12779351.

Shao, Hue et al., "Single-Cell Detection Using Optofluidic Intracavity Spectroscopy", IEEE Sensors Journal, vol. 6, No. 6, Dec. 1, 2006.

Chinese Patent Application Publication No. 201280024070.X Office Action dated Mar. 26, 2015, 7 pages.

Japan Patent Application No. 2014-509389 Official Action dated Feb. 22, 2016, 2 pages.

* cited by examiner

MULTI-SPOT COLLECTION OPTICS

RELATED APPLICATIONS

This application is a 371 of PCT Application number PCT/US2012/036137, filed May 2, 2012, which claims the benefit of U.S. Provisional Application No. 61/481,886, filed May 3, 2011, which are hereby incorporated by reference in its entirety.

FIELD OF THE INVENTION

The present invention relates generally to optical sensing, and specifically to collecting and sensing optical emission from an array of spots.

BACKGROUND

In some methods and systems of inspection that are known in the art, a sample is induced to emit radiation from an array of spots. For instance, multiple excitation beams may be directed toward the sample in a predetermined geometrical pattern, and the resulting emission from each of the spots on which a beam is incident may then be collected and measured. Such multi-spot configurations can be useful in increasing inspection throughput since multiple locations are inspected in parallel.

As one example of such a system, U.S. Pat. No. 6,465,783, whose disclosure is incorporated herein by reference, describes apparatus and methods for inspecting semiconductor wafers and other types of specimens using parallel charged particle beams, such as electron beams. An emitter array produces multiple beams that propagate along respective beam axes. The beams pass simultaneously through projection lenses and a deflector so as to cause the beams to be focused simultaneously onto respective loci on the surface of the specimen, thus causing each locus to emit secondary electrons. The secondary electrons are detected by a secondary-electron (SE) array including multiple SE-detector units. Each SE detector unit receives and detects secondary electrons emitted from a respective locus.

As another example, PCT International Publication WO 2003/041109, whose disclosure is incorporated herein by reference, describes a high data-rate electron beam spot-grid array imaging system. Embodiments include an imaging system comprising an electron beam generator for simultaneously irradiating an array of spots spaced apart from each other on a surface of an object to be imaged. A detector collects backscattered and/or secondary electrons emitted as a result of the interaction of the spots with the surface of the object to form an image of the irradiated portions of the object surface. A mechanical system moves the substrate in a direction which is nearly parallel to an axis of the array of spots such that as the substrate is moved across the spot array in the scan direction, the spots trace a path which leaves no gaps in the mechanical cross-scan direction.

Other spot-grid array systems, using charged particle or optical excitation beams, are described in PCT International Publication WO 2005/024881 and in U.S. Patent Application Publication 2006/0261261, whose disclosures are likewise incorporated herein by reference.

SUMMARY

Embodiments of the present invention that are described hereinbelow provide apparatus and methods for efficiently collecting and detecting optical radiation from an array of spots on an object.

There is therefore provided, in accordance with an embodiment of the present invention, apparatus for detecting optical radiation emitted from an array of spots on an object. The apparatus includes a plurality of light guides having respective input ends and output ends, with the input ends ordered in a geometrical arrangement corresponding to the array of the spots. Relay optics are configured to collect and focus the optical radiation from the object onto the input ends such that each input end receives the optical radiation from a corresponding one of the spots. Multiple detectors are each coupled to receive the optical radiation from an output end of a respective one of the light guides.

In some embodiments, the geometrical arrangement includes a two-dimensional grid, which may be hexagonal. Typically, the light guides include optical fibers, whose input ends may be closely packed together to form a fiber bundle in the geometrical arrangement. Alternatively or additionally, the relay optics include a microlens array, which includes multiple microlenses disposed in the geometrical arrangement of the light guides so that each microlens focuses the optical radiation onto the input end of a corresponding one of the light guides.

In a disclosed embodiment, the relay optics include a zoom lens, having a magnification that is variable so as to adjust for variations in a spacing of the array of the spots. Additionally or alternatively, the geometrical arrangement of the input ends is rotatable so as to adjust for rotation of the array of the spots.

In one embodiment, the apparatus includes an alignment unit, which is configured to form an image of the array of the spots on the object superimposed with optical radiation transmitted through at least some of the light guides from the respective output ends to the respective input ends and projected onto the object through the relay optics.

In another embodiment, the apparatus includes an alignment unit, which includes a fiber bundle integrated with the light guides. The fiber bundle includes one or more optical fibers and has an input end arranged to receive the optical radiation from one of the spots. An alignment detector is coupled to receive the optical radiation emitted from the output end of the fiber bundle and to generate signals indicative of an alignment of the fiber bundle with the one of the spots. A controller is configured to adjust the relay optics responsively to the signals. Typically, the alignment detector includes multiple detector elements, which output respective signals, and the fiber bundle includes multiple optical fibers, which are arranged so that a deviation in the alignment of the fiber bundle with the one of the spots causes changes in the respective signals that are indicative of the deviation.

Additionally or alternatively, the alignment unit includes multiple fiber bundles and multiple alignment detectors, each coupled to receive the optical radiation from a respective one of the fiber bundles and to provide the signals to the controller.

In a disclosed embodiment, the object includes a scintillator, which is configured to emit the optical radiation from the spots in response to corresponding beams of secondary electrons that are emitted from respective locations on a sample and focused onto the scintillator. The apparatus may also include an electron source, which is configured to direct multiple beams of primary electrons toward the respective locations on the sample so as to cause the sample to emit the secondary electrons.

There is also provided, in accordance with an embodiment of the present invention, a method for detecting optical radiation emitted from an array of spots on an object. The method includes arranging a plurality of light guides, having respective input ends and output ends, so that the input ends are ordered in a geometrical arrangement corresponding to the array of the spots. The optical radiation is collected and focused from the object onto the input ends so that each input end receives the optical radiation from a corresponding one of the spots. The optical radiation transmitted through the light guides is detected using a respective detector coupled to an output end of each of the light guides.

The present invention will be more fully understood from the following detailed description of the embodiments thereof, taken together with the accompanying drawings.

BRIEF DESCRIPTION OF THE DRAWINGS

The present invention is illustrated by way of example, and not limitation, in the figures of the accompanying drawings, in which.

DETAILED DESCRIPTION

In inspection systems that use spot-grid arrays, such as those described in the Background section above, it is necessary to efficiently collect and measure the optical radiation emitted from multiple spots in parallel. (The term "optical radiation," in the context of the present patent application and in the claims, refers to electromagnetic radiation in the visible, ultraviolet, or infrared spectral range.) The emitted radiation is often weak, and it is therefore desirable to use an individual, sensitive detector, such as a photomultiplier tube (PMT), for each spot.

Embodiments of the present invention that are described hereinbelow provide optical systems that are useful in this context, for efficiently collecting radiation from an array of spots on an object and conveying the radiation from each spot to its respective detector. These embodiments use a bundle of light guides, such as optical fibers, whose input ends are ordered in a geometrical arrangement that corresponds to the geometry of the array of spots. Typically, the geometry is a two-dimensional grid, meaning an ordered array in which the spots are spaced apart along well-defined lines (including, but not limited to, rectangular grids). Alternatively, other one- and two-dimensional ordered arrangements of the spots and light guides may be used. Relay optics collect and focus the radiation from each of the spots onto the corresponding light guide, and a respective detector is coupled to receive and measure the optical radiation transmitted through the output end of each light guide.

This sort of optical arrangement is particularly useful for collecting light emitted from an array of spots on a scintillator, in response to corresponding beams of secondary electrons that are emitted by a sample (such as an e-beam excited semiconductor wafer) and focused onto the scintillator. Alternatively, such optical arrangements may be used to collect optical radiation from spots on the sample itself, which may be irradiated by incident beams of either particles or electromagnetic radiation, for example. Further alternatively, the principles of the present invention may be applied in collecting and detecting optical radiation emitted from substantially any suitable ordered array of loci. The term "spots" should therefore be understood, in the context of the present patent application and in the claims, as referring to any set of predefined loci that emit optical radiation, whether by fluorescence (as in the case of a scintillator), reflection, scattering, or any other emission mechanism.

Figure 1:
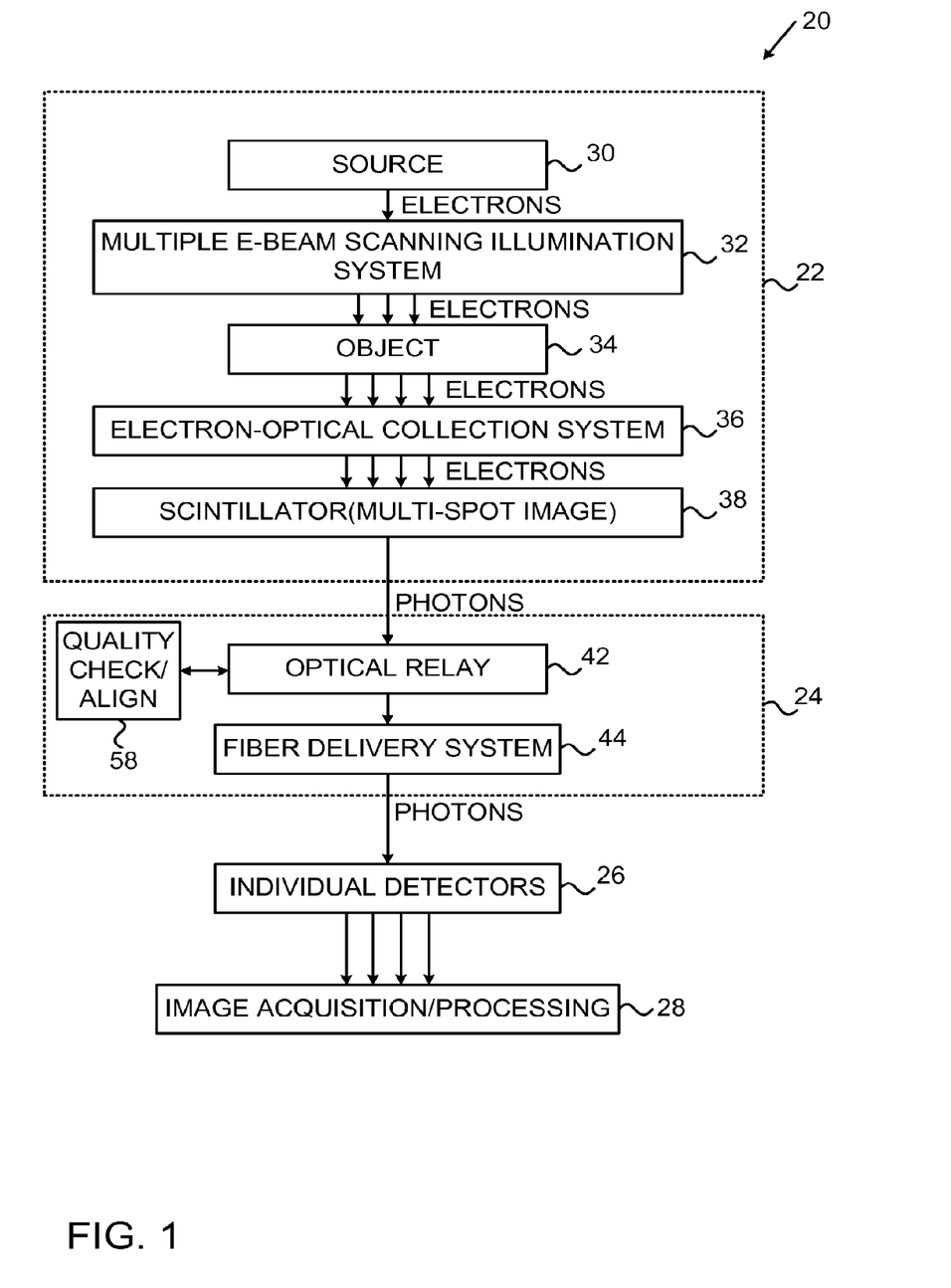
FIG. 1 is a block diagram that schematically illustrates a system for inspection of a sample, in accordance with an embodiment of the present invention.

FIG. 1 is a block diagram that schematically illustrates a system 20 for inspection of a sample 34, in accordance with an embodiment of the present invention. The system comprises an e-beam module 22, which creates a multi-spot image on a scintillator 38. An optical module 24 collects photons from each of the spots and conveys them to individual detectors 26. An image acquisition and processing unit 28, typically a computer with suitable input circuits, receives and processes the detector signals in order to extract information concerning the object. For example, sample 34 may comprise a semiconductor wafer, and unit 28 may analyze the detector outputs in order to identify defects in the wafer.

The operation of module 22 is beyond the scope of the present patent application. Such modules are known in the art, as described, for example, in the references cited in the Background section above. Briefly stated, an electron source 30 is coupled to a scanning subsystem 32 in order to generate multiple beams of electrons, which are scanned simultaneously across the surface of object 34. Typically, the beam energy may be varied depending upon application requirements. The incident beams cause the object to emit secondary electrons, which are collected and imaged by an electron-optical collection subsystem 36 onto scintillator 38. At each spot where the electrons strike the scintillator, the scintillator emits light of intensity that is proportional to the local electron flux. The components of module 22 are typically contained in a vacuum chamber, with a window adjacent to the scintillator.

Figure 2:
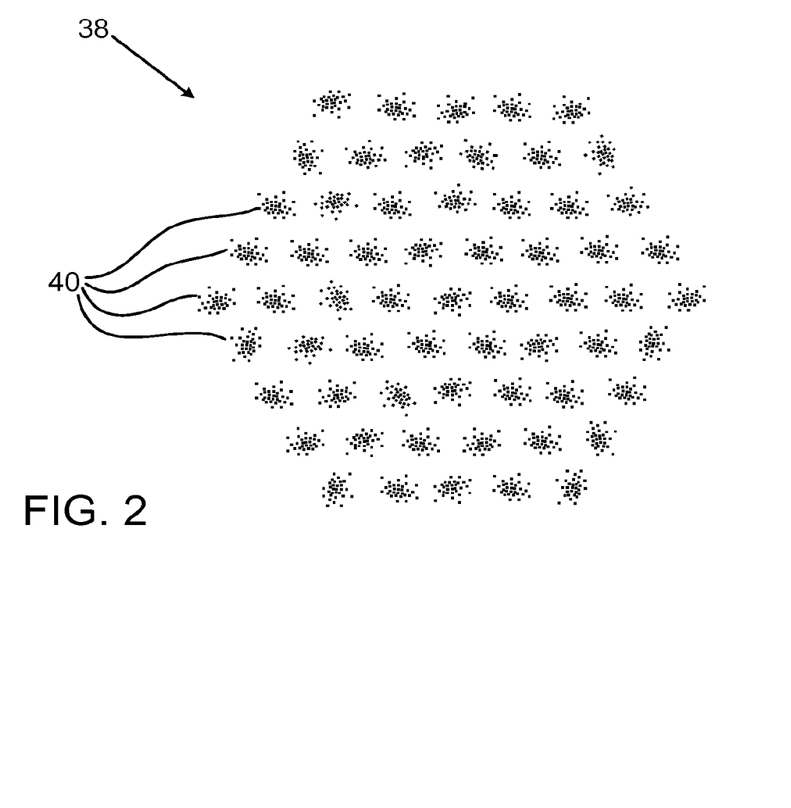
FIG. 2 is a schematic, frontal view of a spot-grid array, in accordance with an embodiment of the present invention.

FIG. 2 is a schematic, frontal view of the spot-grid array that is formed on scintillator 38, in accordance with an embodiment of the present invention. In this example, the array comprises spots 40, arranged in a hexagonal grid pattern. Alternatively, larger or smaller girds may be used, in both hexagonal and other geometrical patterns. (For convenience of representation, FIG. 2 is a negative of the actual image, i.e., the bright spots appear dark in FIG. 2, while the dark background appears white.) It is desirable that collection subsystem 36 focus the secondary electrons onto the scintillator sufficiently sharply so that spots 40 are clearly separated, with most of the energy of each spot confined within a diameter that is less that the pitch of the array. Typically, in the system of FIG. 1, the pitch of spots 40 on scintillator 38 is on the order of 100-200 μm. Both the pitch and the rotation angle of the spot grid may change when the energy of the e-beam that is incident on object 34 varies.

Returning now to the elements of optical module 24 in FIG. 1, an optical relay 42 focuses the photons emitted from the array of spots on scintillator 38 into corresponding optical fibers in a fiberoptic delivery subsystem 44. The fibers deliver the photons to the individual detectors 26. Relay 42 and delivery subsystem 44 are adjustable, as described in detail hereinbelow, in order to accommodate possible changes in the pitch and rotation angle of the spot grid on scintillator 38. A beam quality and alignment unit 58 monitors these changes and may provide adjustment signals to the optical relay, as described in greater detail hereinbelow.

Figure 3:
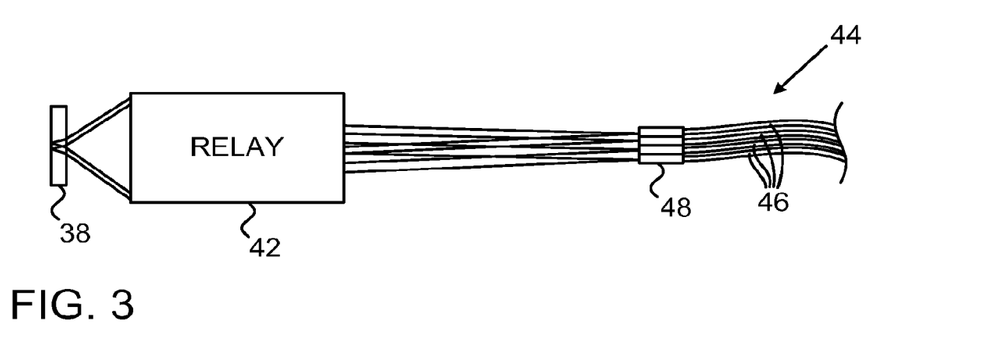
FIG. 3 is a simplified schematic view of an optical module, in accordance with an embodiment of the present invention.

FIG. 3 is a schematic side view of optical module 24, in accordance with an embodiment of the present invention. Fiber delivery subsystem 44 comprises fibers 46, which are closely packed together at their input ends, so that adjacent fiber claddings are in physical contact to form a bundle 48 in an ordered arrangement (a hexagonal grid in the present example) that matches the arrangement of spots 40 on scintillator 38. Typically, glass or fused silica fibers (rather than plastic) are used in this sort of embodiment to ensure that the pitch of the bundle is precise and uniform. The fibers in bundle 48, for example, may have a pitch between 0.8 and 1.0 mm and an input numerical aperture (NA) between 0.1 and 0.2. Consequently, relay 42 has a magnification between about 4× and 10×, in order to match the pitch of spots 40 on scintillator 38 to that of bundle 48.

Figure 4:
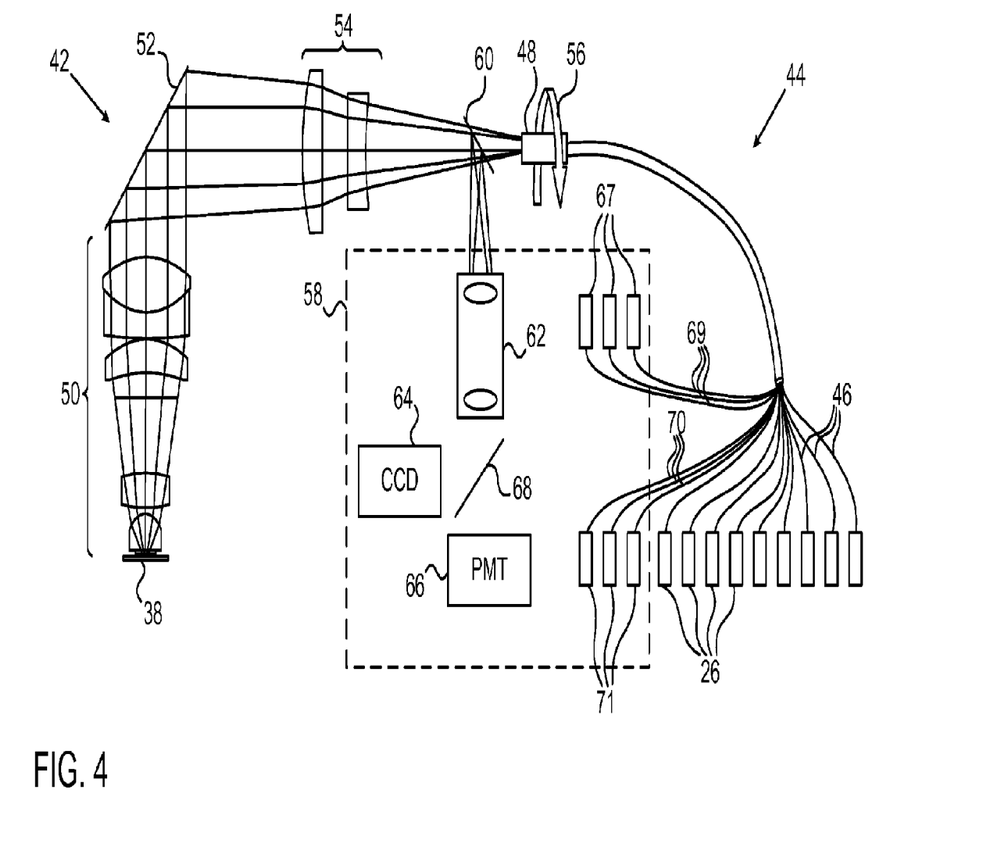
FIG. 4 is a schematic side view of an optical module and detectors, in accordance with an embodiment of the present invention.

FIG. 4 is a schematic side view showing further details of optical module 24, in accordance with an embodiment of the present invention. Relay optics 42 comprise an objective 50, which collects the light from scintillator 38. A folding mirror 52 directs the collected beams through a zoom lens 54. The zoom lens varies the magnification of the relay optics as required. A rotation stage 56 or other suitable rotation mechanism rotates bundle 48 to accommodate rotation of the array of the array of spots on scintillator 38. The output end of each fiber 46 is coupled to a respective detector 26. As noted earlier, the optical module also includes beam quality/alignment unit 58, which is described in greater detail hereinbelow.

Figure 5:
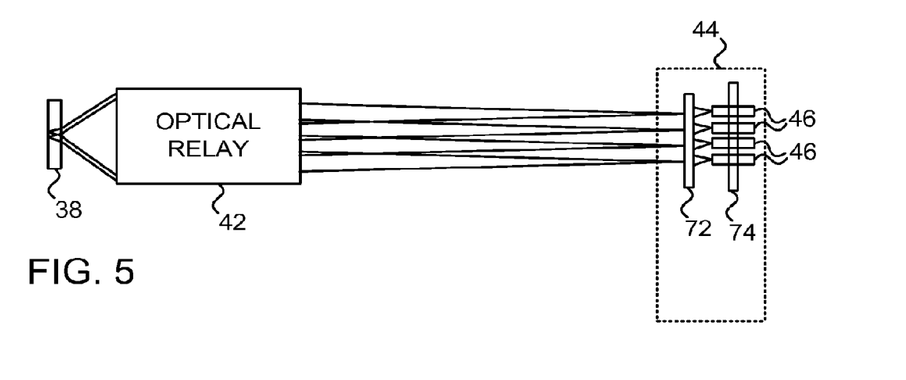
FIG. 5 is a simplified schematic view of an optical module, in accordance with an alternative embodiment of the present invention.
Figure 6:
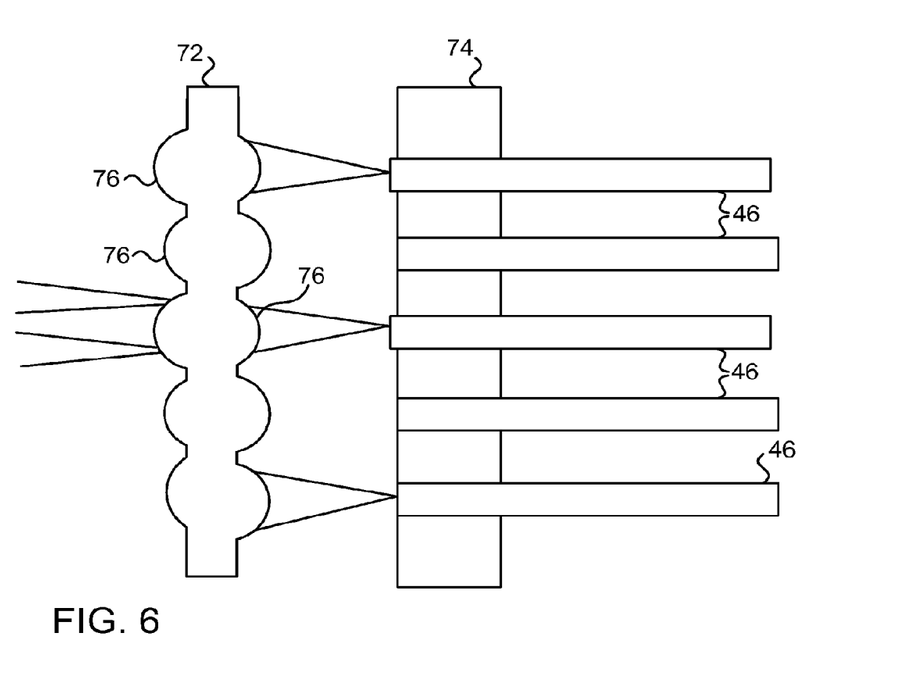
FIG. 6 is a schematic side view showing details of an optical module, in accordance with an alternative embodiment of the present invention.

Reference is now made to FIGS. 5 and 6, which schematically illustrate elements of optical module 24, in accordance with an alternative embodiment of the present invention. FIG. 5 is a simplified side view of the module, while FIG. 6 shows details of the optics. In this embodiment, fiber delivery subsystem 44 comprises a microlens array (MLA) 72, which comprises microlenses 76 arranged in the same geometrical grid pattern as fibers 46 and spots 40. Each microlens focuses the light from one of the spots onto the input end of a corresponding one of the fibers, which are held in position by a plate 74. The plate is used in this embodiment to hold the fibers in position at a pitch equal to that of the MLA, which is typically about 2 mm.

Because of the relatively larger pitch between fibers, relay 42 must generally have higher magnification (typically on the order of 10×-20×, depending on electron energy) than the relay in the embodiment of FIGS. 3 and 4. Furthermore, because of the short focal length of microlenses 76, fibers 46 should typically have a large NA, on the order of 0.3 to 0.4, in order to match the output NA of the microlenses.

On the other hand, the embodiment of FIGS. 5 and 6 has the advantage of being able to match any known geometrical distortion of the spot pattern on scintillator 38. For example, aberrations of the electron optics in system 20 may cause barrel or pincushion distortion of the spot grid. In such cases, MLA 72 and plate 74 may be manufactured with the same distortion as the spot grid: MLA 72 may be suitably produced on a glass blank using a photolithographic technique, for example, while plate 74 is made by precision drilling (such as laser drilling) in a metal or ceramic substrate. The ability to match the MLA and plate to the spot pattern is particularly useful when the grid contains a large number of spots. The use of plate 74 to hold fibers 46 also relaxes the dimensional tolerance of the fibers themselves, so that plastic fibers may be used instead of the glass fibers in the embodiment of FIGS. 3 and 4.

Returning now to FIG. 4, one way to align fibers 46 in bundle 48 with the spots on scintillator 38 is for a beamsplitter 60 to direct light emitted from the scintillator into alignment unit 58. (The beamsplitter may be fixed or retractable.) Imaging optics 62 form an image of the scintillator surface on an image sensor 64, such as a charge-coupled device (CCD). Optionally, the light may also be directed, via a beamsplitter 68, onto a PMT 66 or other sensitive radiation detector, which may be used if an overall power measurement is needed, and specifically if a single spot is "turned on" when aligning the system.

At the same time, alignment light sources 67 may be operated either to reverse-illuminatesome or all of fibers 46 (by coupling the light sources to the respective output ends of these fibers) or to illuminate dedicated back-illumination fibers 69, as shown in FIG. 4. Typically, at least three fibers are reverse-illuminated in this manner. The light is transmitted backward to the input end of bundle 48 and is projected onto the scintillator surface by relay optics 42.

Figure 7:
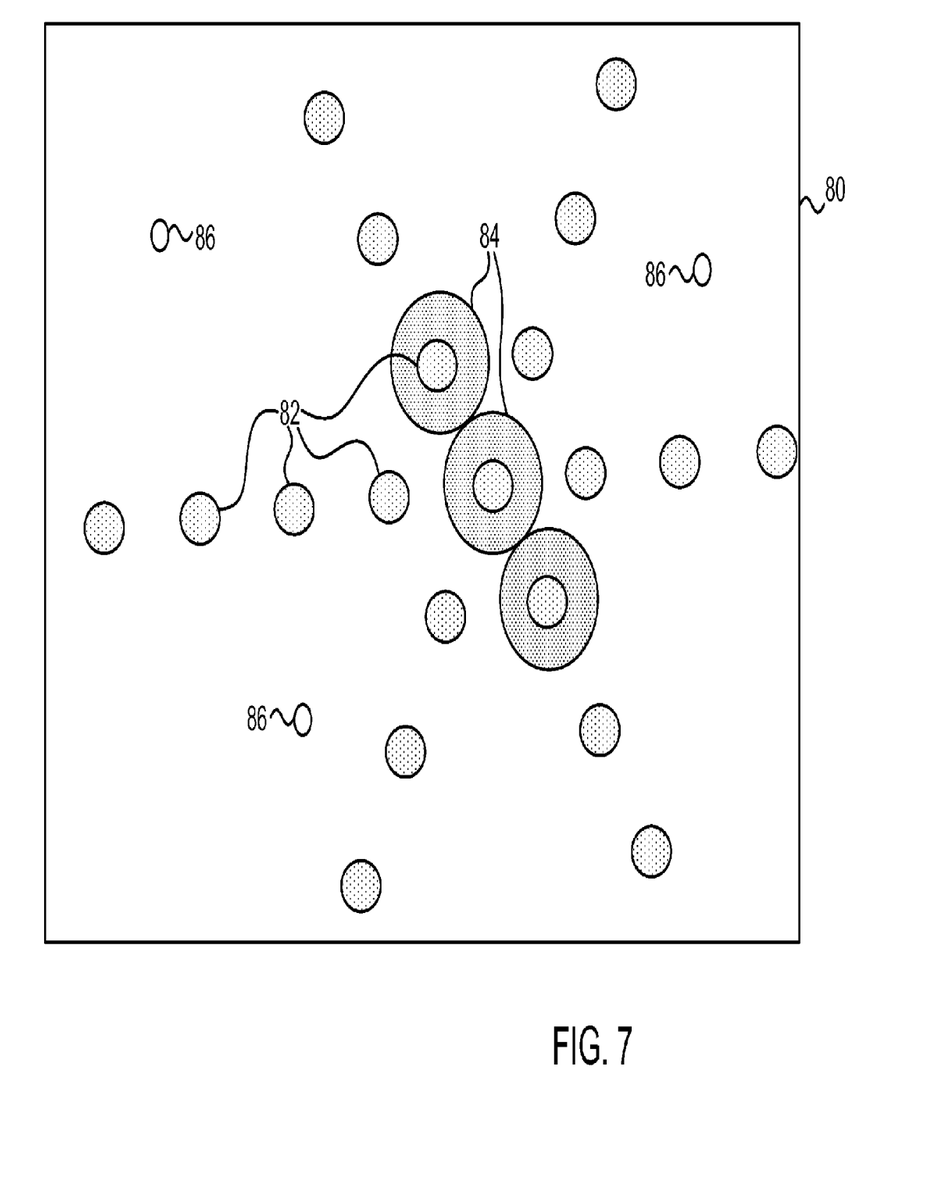
FIG. 7 is a schematic representation of an image formed by an alignment unit, in accordance with an embodiment of the present invention.

FIG. 7 is a schematic representation of an alignment image 80 formed by image sensor 64 using the technique described above, in accordance with an embodiment of the present invention. (Like FIG. 2, this is a negative of the actual image.) Spots 82 are formed by incidence of electrons on scintillator 38 and correspond to the locations of spots 40 in the embodiments described above, although the spot pattern used in the present example is different from that shown in FIG. 2. Larger spots 84 are formed on the scintillator by the light that has been back-transmitted through fiber bundle 48. The overlap between spots 84 and the corresponding spots 82 shows that fiber bundle 48 is properly aligned with the spot-grid array. In case of misalignment, zoom lens 54 and/or rotation stage 56 may be adjusted until spots 84 are properly positioned in the alignment image. This alignment process may be repeated at different electron energies in order to determine the appropriate compensation for the changes in pitch and angle of the spot grid.

Whereas the methods described above are useful particularly in initial alignment of optical module 24, quality monitoring fiber bundles 70 and alignment detectors 71 (FIG. 4) may be used, additionally or alternatively, to detect and compensate for deviations from alignment that may occur both prior to and during operation of system 20. Fiber bundles 70 are typically integrated with fibers 46 in bundle 48. Deviations may arise during operation due to optical, mechanical, or electrical instabilities, for example, which can cause fibers 46 to lose alignment with their respective spots 40 on scintillator 38. Detectors 71 provide rapid feedback to stabilize relay optics 42 (with typical loop bandwidth between 1 and 100 kHz) by adjusting factors including the magnification, rotation, shift, and astigmatic distortion of the optical beams that are focused onto bundle 48.

For the purposes of detectors 71, e-beam module 22 may be operated to create additional guidance spots 86 (FIG. 7)

not only during the initial alignment phase, but also during normal operation of system 20, as part of the spot-grid array on scintillator 38. Alternatively, spots 86 may be produced on the scintillator by other means. Guidance spots 86 may be outside the measurement area of the sample and may have much smaller intensity than spots 40. It is desirable that there be at least three guidance spots 86 on scintillator 38, in non-collinear locations. Any shift, rotation, or distortion in spots 40 will be reflected in similar changes to spots 86 and may be corrected by adjusting relay optics 42 to return spots 86 to alignment with bundles 70.

In an alternative embodiment (not shown in the figures), alignment detectors 71 may receive light from their respective spots via beamsplitter 60, rather than from quality monitoring fiber bundles 70. As a further alternative, image sensor 64 may be used for this purpose.

Figure 8:
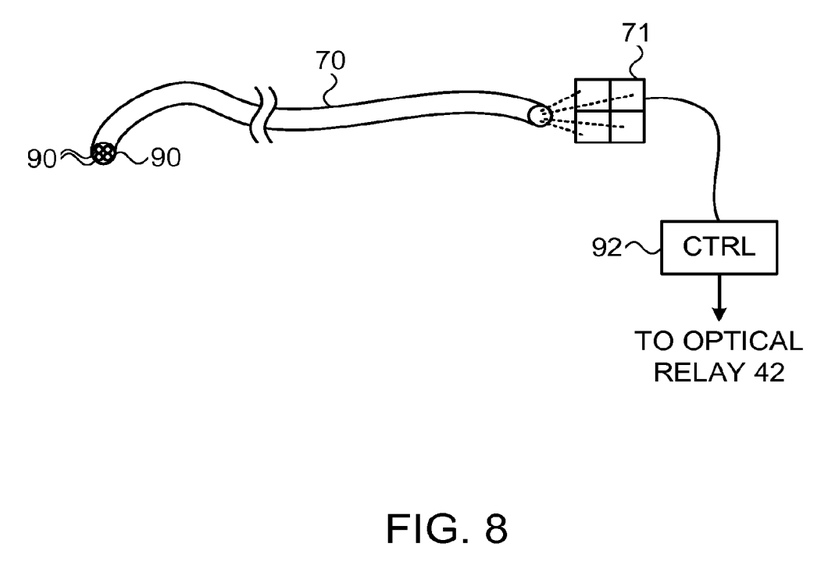
FIG. 8 is schematic, pictorial view of a guidance spot monitoring element, in accordance with an embodiment of the present invention.

FIG. 8 is schematic, pictorial view of a guidance spot monitoring unit, in accordance with an embodiment of the present invention. This unit comprises one of fiber bundles 70 and the corresponding detector 71, which are shown in FIG. 4. As explained above, each such fiber bundle 70 is aligned at its input end with a respective guidance spot 86 via relay optics 42, while the output end of bundle 70 feeds detector 71. This detector typically comprises multiple detector elements. Thus, in the pictured example, detector 71 is a four-quadrant detector, and bundle 70 comprises four fibers 90, each of which feeds a respective quadrant of the detector. Alternatively, bundle 70 may comprise a larger number of fibers in a coherent arrangement, and detector 71 may comprise an image sensor, such as a CCD or CMOS sensor, which thus receives and senses an image of spot 86.

When optical module 24 is properly aligned, the image of spot 86 formed by relay optics 42 is centered on the input end of bundle 70, and thus all quadrants of detector 71 receive roughly equal optical signals. When a deviation from alignment occurs, however, the quadrant signals will become unbalanced. A controller 92 detects the signals from detectors 71 and thus senses the deviation from alignment that has occurred. By comparing the signals from the different detectors, the controller can distinguish whether a rotation, magnification change, or linear shift has occurred. Controller 92 outputs a correction signal accordingly to the appropriate component of the relay optics, such as zoom lens 54 or stage 56 (FIG. 4). In this manner, proper alignment is maintained dynamically without disturbing the normal operation of system 20.

Detector 71 (in the form of a quadrant or array detector) can also provide information regarding astigmatism of spots 86, and hence of spots 40. Such astigmatism may cause the spots to be elliptically elongated along one of the diagonal directions. In this case, the two quadrants on the diagonal will give larger signals, while the off-diagonal quadrants will give smaller signals. The astigmatism may be corrected, for example, by introducing a small orthogonal astigmatism in the electron optics or relay optics.

In another embodiment, each detector 71 may comprise a single detector element (and each fiber bundle 70 may then comprise a single fiber or an incoherent bundle of fibers). To detect changes in alignment, a small, periodic deviation may be introduced in the positions of spots 40 and 86, by modulating the electron beam, for example. Changes in alignment will then appear as changes in the time-dependence of the signals output by detector 71.

Although the use of guidance spots and monitoring elements is described above with reference to the spot-grid array of system 20, the principles of this embodiment may similarly be applied in maintaining alignment of scanning-beam systems.

Furthermore, although the examples mentioned above refer specifically to spot-grid array detection systems, in the particular context of semiconductor wafer inspection, the principles of the present invention may similarly be applied in any suitable sort of application that involves measurement of optical radiation that is emitted from an array of spots. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. An apparatus for detecting optical radiation emitted from an array of spots on an object resulting from multiple excitation beams incident on the object, the apparatus comprising:
   a plurality of light guides having respective input ends and output ends, with the input ends ordered in a geometrical arrangement corresponding to the array of spots;
   relay optics, configured to collect and focus the optical radiation from the array of spots on the object onto the input ends such that each input end receives the optical radiation from a corresponding one of the spots;
   multiple detectors, each detector coupled to receive the optical radiation from a respective output end of a respective one of the light guides; and
   an alignment unit configured to monitor changes in pitch and rotation angle of the array of spots resulting from changes in energy of the multiple excitation beams, wherein the changes in rotation angle occur about an axis normal to the surface of the object, wherein the alignment unit is further configured to, in response to detecting the changes, generate signals indicative of an alignment of the plurality of light guides with the array of spots.

2. The apparatus according to claim 1, wherein the geometrical arrangement comprises a hexagonal grid.

3. The apparatus according to claim 1, wherein the light guides comprise optical fibers.

4. The apparatus according to claim 3, wherein the input ends are closely packed together to form a fiber bundle in the geometrical arrangement.

5. The apparatus according to claim 1, wherein the relay optics comprise a microlens array having multiple microlenses disposed in the geometrical arrangement of the light guides so that each microlens focuses the optical radiation onto a respective input end of a corresponding one of the light guides.

6. The apparatus according to claim 1, wherein the relay optics comprise a zoom lens, having a magnification that is variable so as to adjust for variations in a spacing of the array of the spots.

7. The apparatus according to claim 1, wherein the geometrical arrangement of the input ends is rotatable so as to adjust for rotation of the array of the spots.

8. The apparatus according to claim 1, wherein the alignment unit is further configured to form an image of the optical radiation emitted from the array of spots on the object superimposed with additional optical radiation transmitted through at least some of the light guides from respective output ends of each of the light guides to respective input ends of the light guides and projected onto the object through the relay optics.

9. The apparatus according to claim 1, wherein the alignment unit comprises:
a fiber bundle integrated with the light guides, the fiber bundle, comprising one or more optical fibers, having an input end arranged to receive the optical radiation from one of the spots and having an output end;
an alignment detector, which is coupled to receive the optical radiation emitted from the output end of the fiber bundle and to generate the signals, wherein the signals are indicative of an alignment of the fiber bundle with the one of the spots; and
a controller, which is configured to adjust the relay optics responsively to the signals.

10. The apparatus according to claim 9, wherein the alignment detector comprises multiple detector elements, which output respective signals, and wherein the fiber bundle comprises multiple optical fibers, which are arranged so that a deviation in the alignment of the fiber bundle with the one of the spots causes changes in the respective signals that are indicative of the deviation.

11. The apparatus according to claim 9, wherein the alignment unit comprises multiple fiber bundles and multiple alignment detectors, each coupled to receive the optical radiation from a respective one of the fiber bundles and to provide the signals to the controller.

12. The apparatus according to claim 1, wherein the object comprises a scintillator, which is configured to emit the optical radiation from the spots in response to corresponding beams of secondary electrons that are emitted from respective locations on a sample and focused onto the scintillator.

13. The apparatus according to claim 12, further comprising an electron source, which is configured to direct multiple beams of primary electrons toward the respective locations on the sample so as to cause the sample to emit the secondary electrons.

14. A method for detecting optical radiation emitted from an array of spots on an object resulting from multiple excitation beams incident on the object, the method comprising:
collecting and focusing the optical radiation from the array of spots on the object input ends of a plurality of light guides, the input ends being ordered in a geometrical arrangement corresponding to the array of the spots, so that each input end receives the optical radiation from a corresponding one of the spots;
detecting the optical radiation transmitted through the light guides using a respective detector coupled to a respective output end of each of the light guides; and
monitoring changes in pitch and rotation angle of the array of spots resulting from changes in energy of the multiple excitation beams, wherein the changes in rotation angle occur about an axis normal to the surface of the object, wherein the alignment unit is further configured to, in response to detecting the changes, generating signals indicative of an alignment of the plurality of light guides with the array of spots.

15. The method according to claim 14, wherein focusing the optical radiation comprises directing the collected optical radiation through a microlens array, which comprises multiple microlenses disposed in the geometrical arrangement of the input ends of the light guides, so that each microlens focuses the optical radiation onto a respective input end of a corresponding one of the light guides.

16. The method according to claim 14, wherein focusing the optical radiation comprises applying a zoom lens, having a magnification that is variable, to the optical radiation so as to adjust for variations in a spacing of the array of the spots.

17. The method according to claim 14, further comprising arranging the plurality of the light guides by rotating the geometrical arrangement of the input ends so as to adjust for rotation of the array of the spots.

18. The method according to claim 14, further comprising aligning the light guides by forming an image of the optical radiation emitted from the array of spots on the object superimposed with additional optical radiation transmitted through at least some of the light guides from the respective output ends to the respective input ends and projected onto the object through relay optics.

19. The method according to claim 14, further comprising aligning the light guides by:
arranging an input end of a fiber bundle, which comprises one or more optical fibers and is integrated with the light guides, to receive the optical radiation from one of the spots;
directing the optical radiation from an output end of the fiber bundle onto an alignment detector, which generates signals indicative of an alignment of the fiber bundle with the one of the spots; and
adjusting relay optics responsively to the signals.

20. The method according to claim 19, wherein arranging the input end of the fiber bundle comprises arranging multiple fiber bundles, which direct the optical radiation onto multiple respective alignment detectors, and wherein the relay optics are adjusted responsively to the signals from the at least three of the multiple respective alignment detectors.

* * * * *